United States Patent [19]

Okuyama et al.

[11] Patent Number: 5,676,970
[45] Date of Patent: Oct. 14, 1997

[54] ANTI-INFLAMMATORY ANALGESIC PLASTER

[75] Inventors: Hirohisa Okuyama, Tomisato-machi; Yasuo Ikeda, Narashino; Shigenori Otsuka, Chiba; Shuichi Kasai, Narita; Akira Iwasa, Yotsukaido, all of Japan

[73] Assignee: SS Pharmaceutical Co., Ltd., Tokyo, Japan

[21] Appl. No.: 541,089

[22] Filed: Oct. 11, 1995

Related U.S. Application Data

[63] Continuation of Ser. No. 218,183, Mar. 28, 1994, abandoned.

[30] Foreign Application Priority Data

Mar. 29, 1993 [JP] Japan .................. 5-069895

[51] Int. Cl.$^6$ .................. A61F 13/00; A61K 9/70
[52] U.S. Cl. .................. 424/449; 106/778
[58] Field of Search .................. 424/449; 106/778

[56] References Cited

U.S. PATENT DOCUMENTS

| | | | |
|---|---|---|---|
| 4,666,716 | 5/1987 | Sheth et al. | 424/195.1 |
| 4,695,465 | 9/1987 | Kigasawa et al. | 424/449 |
| 4,778,799 | 10/1988 | Tibes et al. | 514/277 |
| 4,952,560 | 8/1990 | Kigasawa et al. | 514/2 |
| 5,254,338 | 10/1993 | Sakai et al. | 424/78.35 |
| 5,292,461 | 3/1994 | Juch et al. | 264/37 |

FOREIGN PATENT DOCUMENTS

| | | |
|---|---|---|
| A-0276561 | 8/1988 | European Pat. Off. . |
| A-0592123 | 3/1993 | European Pat. Off. . |

OTHER PUBLICATIONS

Database WPI Week 9125 Derwent Pulications Ltd., London, GB; AN 91–181416 & JP–A–3 109 327 (Maeda Yakuhin Kogyo et al) May 9, 1991, Abstract.

Database WPI Week 9025, Derwent Publications Ltd., London, GB; AN 90–189690 & JP–A–2 124821 (Toyama Chem KK) 14 May 1990, Abstract.

Patent Abstracts of Japan, vol. 14, No. 115, (C–0696) Mar. 5, 1990 & JP–A–01 316 314 (Taisho Pharmaceutical Co. Ltd.) Dec. 21, 1989, Abstract.

*Primary Examiner*—Helen Lee
*Attorney, Agent, or Firm*—Oblon, Spivak, McClelland, Maier & Neustadt, P.C.

[57] ABSTRACT

An anti-inflammatory analgesic plaster carries thereon a base which comprises piroxicam and a polyoxyethylene nonionic surfactant having 5–15 moles of added ethylene oxide.

10 Claims, 2 Drawing Sheets

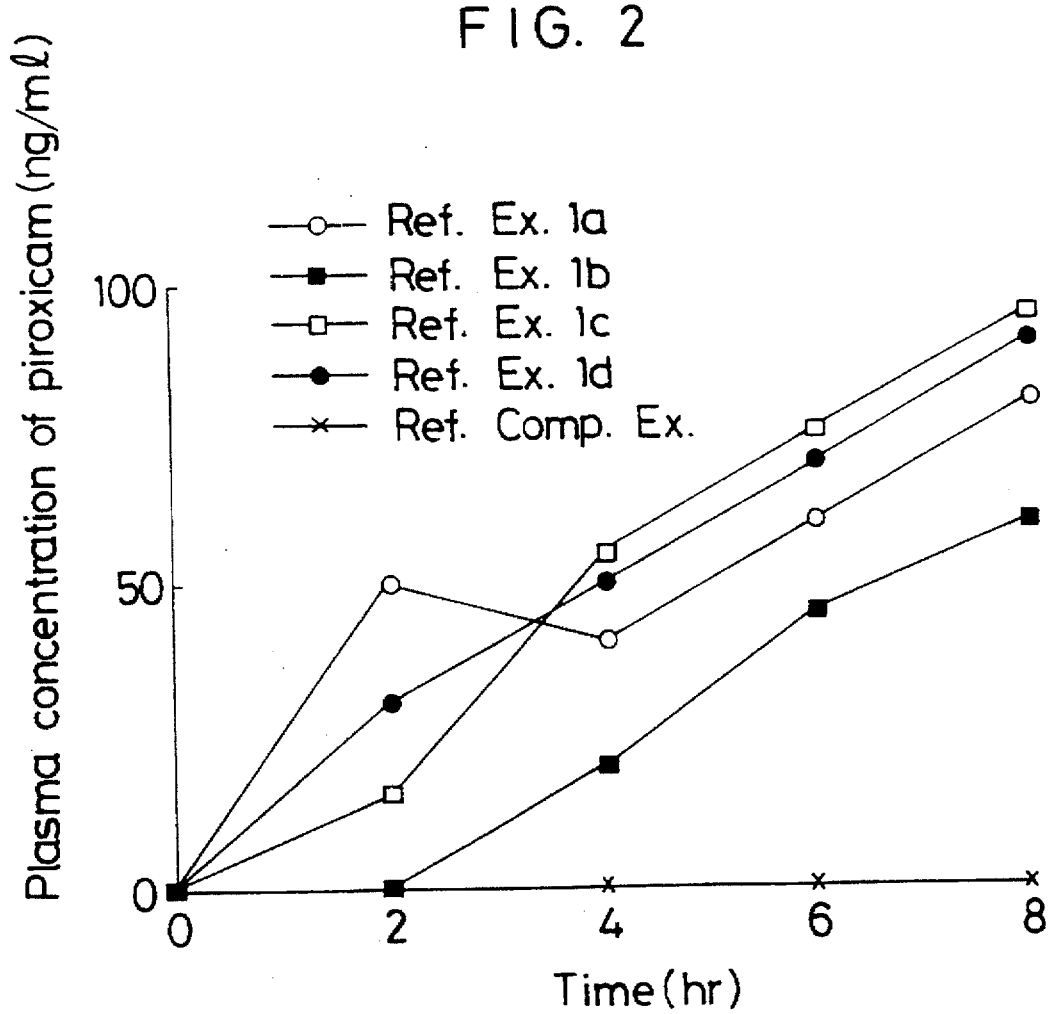

ANTI-INFLAMMATORY ANALGESIC PLASTER

This application is a continuation of application Ser. No. 08/218,183, filed on Mar. 28, 1994, now abandoned.

BACKGROUND OF THE INVENTION

1. Field of the Invention

This invention relates to a plaster having excellent percutaneous absorption of piroxicam and high anti-inflammatory and analgesic effects.

2. Description of the Related Art

Piroxicam is useful as an anti-inflammatory analgesic and has found wide-spread clinical utility as oral preparations for rheumatoid arthritis, osteoarthritis, low back pain, cervico-omo-brachial syndrome and the like. It is also used as suppositories and ointments.

When administered in the form of oral preparations or suppositories, piroxicam is however reported to cause side effects such as stomatitis, gastric and intestinal pain, gastric heaviness, anorexia, nausea, vomiting, diarrhea and soft stool, in addition to serious side effects such as peptic ulcer associated with perforation, gastrointestinal problems hematemesis and bloody stool and shock symptoms.

To efficiently supply this drug to diseased area without such side effects, it is preferred to allow the drug to percutaneously reach such diseased area without taking the digestive tract. Representative examples of preparations intended for percutaneous absorption include ointments and plasters. As piroxicam-containing ointments, gel-type ointments containing alcohol and water have already been provided for clinical use. An ointment is however accompanied by the drawbacks that the rate of application is unavoidably inaccurate for its inherent nature and after application, the ointment adheres to clothing or the like and is hence lost from the skin.

A plaster, on the other hand, is a good application form, because it is free of such drawbacks and also makes it possible to surely apply an intended amount to the skin for an intended period of time.

Already reported as a piroxicam-containing plaster is a cataplasm with a base comprising 1.0–30.0 wt. % of sodium polyacrylate, 0.01–5.0 wt. % aluminum hydroxide and 30.0–90.0 wt. % of purified water and added with piroxicam or the like [Japanese Patent Application (Kokai) Laid-Open No. HEI 1-316314].

This cataplasm is said to have higher effects compared with cataplasms which are added with a non-steroidal anti-inflammatory analgesic such as indomethacin, diclofenac, flurbiprofen or ketoprofen. However, their percutaneous absorption and the like have not been specifically clarified. It is therefore the current circumstances that no piroxicam-containing cataplasm has been provided yet for clinical use.

There is accordingly a long-standing desire for the provision of a piroxicam-containing anti-inflammatory analgesic plaster which is excellent in actual percutaneous absorption of piroxicam, has high anti-inflammatory analgesic effects and is usable for clinical purposes.

SUMMARY OF THE INVENTION

With the foregoing in view, the present inventors have proceeded with an extensive investigation on the percutaneous absorption of piroxicam and various properties of plasters. As a result, it has been found that the percutaneous absorption of piroxicam can be stabilized and improved irrespective the formulation and pH of the base by combining piroxicam with a specific nonionic surfactant, resulting in the completion of an anti-inflammatory analgesic plaster of good percutaneous absorption according to the present invention. It has also been found that use of a hydrophilic base of pH 5.5–8.0 for the preparation of the anti-inflammatory analgesic plaster can still enhance the percutaneous absorption and at the same time, can provide the anti-inflammatory analgesic plaster with properties ideal as a plaster, that is, with adequate base internal cohesive force and viscoelasticity, strong skin adhesion, good piroxicam stability with time, etc., leading to the completion of the present invention.

A first object of the present invention is therefore to provide an anti-inflammatory analgesic plaster carrying thereon a base which comprises piroxicam and a polyoxyethylene nonionic surfactant having 5–15 moles of added ethylene oxide.

A second object of the present invention is to provide an anti-inflammatory analgesic plaster carrying thereon a hydrophilic base which has a pH of from 5.5 to 8.0 and comprises piroxicam and a polyoxyethylene nonionic surfactant having 5–15 moles of added ethylene oxide.

The plasters according to the present invention are excellent in the percutaneous absorption of piroxicam and also in physical properties as plasters, so that good anti-inflammatory analgesic effects can be obtained. In particular, use of a hydrophilic base whose pH is from 5.5 to 8.0 can provide an anti-inflammatory analgesic plaster having excellent percutaneous absorption of piroxicam and still better physical properties.

BRIEF DESCRIPTION OF THE DRAWINGS

FIG. 2 diagrammatically depicts the percutaneous piroxicam absorptions in terms of the plasma concentration of piroxicam from the piroxicam-containing anti-inflammatory analgesic plasters obtained in Referential Example 1 in comparison with that from a piroxicam-containing anti-inflammatory analgesic plaster obtained in Referential Comparative Example.

DETAILED DESCRIPTION OF THE PREFERRED EMBODIMENTS

Figure 1:
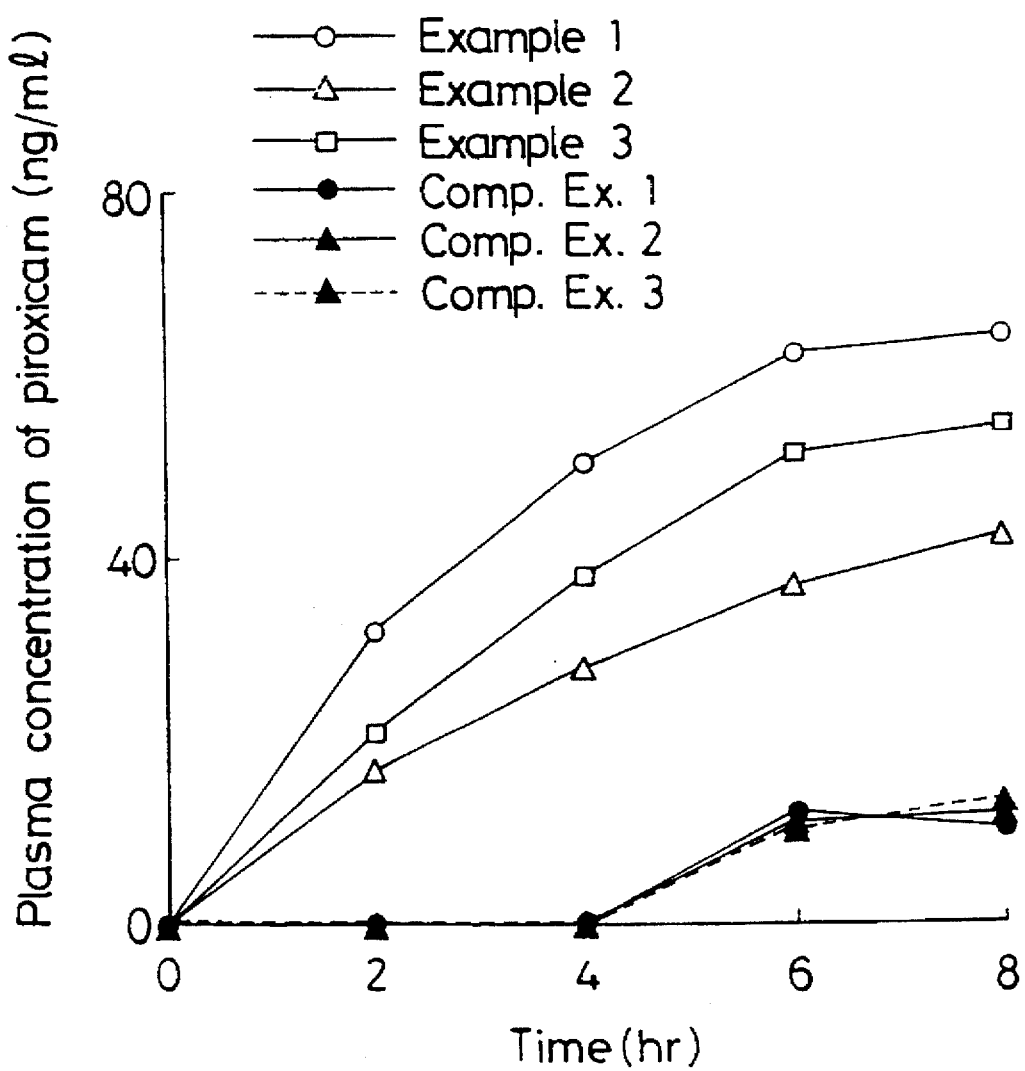
FIG. 1 diagrammatically illustrates the percutaneous piroxicam absorptions in terms of the plasma concentration of piroxicam from the piroxicam-containing anti-inflammatory analgesic plasters obtained in Examples 1–3 in comparison with those from the piroxicam-containing anti-inflammatory analgesic plasters obtained in Comparative Examples 1–3.

Each anti-inflammatory analgesic plaster of the present invention can be obtained by a method known per se in the art, that is, by incorporating piroxicam and the polyoxyethylene nonionic surfactant in a plaster base and then having the resultant plaster base carried on a base material.

Piroxicam, the effective ingredient in the present invention, is incorporated at a concentration of 0.05–5 wt. % (hereinafter indicated simply by "%") in a plaster base (hereinafter called merely the "base"), with 0.1–2% being particularly preferred. Concentrations smaller than 0.05% cannot bring about sufficient effects but even if added at a concentration higher than 5%, no substantial improvement can be observed in effects.

Examples of polyoxyethylene nonionic surfactants usable in the present invention include polyoxyethylene alkyl ethers, polyoxyethylene alkenyl ethers, polyoxy-ethylene fatty acid esters, polyoxyethylene sorbitan fatty acid esters, polyoxyethylene polyoxypropylene alkyl ethers, polyoxyethylene polyoxypropylene alkenyl ethers, polyoxyethylene alkylphenyl ethers, polyoxyethylene hydrogenated castor oil, polyoxyethylene castor oil, and polyoxyethylene sorbitan fatty acid esters. Preferred examples of the alkyl and alkenyl groups in the ether-type surfactants include those containing 10–24 carbon atoms such as decyl, lauryl, myristyl, cetyl, stearyl, arachyl, behenyl, carnaubyl, oleyl, isostearyl and hexadecyl groups. Preferred examples of the acyl groups in the fatty acid ester type surfactants include those having 10–24 carbon atoms such as lauroyl, oleoyl, myristoyl, parmitoyl, stearoyl and behenoyl groups.

In the present invention, the content of the above surfactant in the base may preferably be 1–20% with 2–10% being particularly preferred for the exhibition of the effects. Contents smaller than 1% cannot sufficiently bring about the effects of the present invention, whereas contents greater than 20% cannot substantially improve the effects and are not preferred from the economical standpoint.

The base employed in the present invention preferably has a pH of 5.5–8.0. pH values lower than 5.5 are not preferred because when piroxicam is incorporated, the resulting plasters are observed to undergo color changes with time. In particular, pH values higher than 8.0 are not preferred from the standpoint of skin irritation when it is taken into consideration that plasters are applied continuously. To adjust the pH, a pharmaceutically acceptable acid, alkali or the like can be used.

As the base in the present invention, it is preferred to use a hydrophilic base containing a water-soluble polymer, a divalent or trivalent metal salt or a hydrate thereof and/or a divalent or trivalent metal complex, and water.

The hydrophilic base has not only extremely good percutaneous absorption enhancing effects but also excellent physical properties compared with other hydrophilic bases, whereby excellent drug efficacy can be expected.

As the water-soluble polymer which is one of the components of the above hydrophilic base, a water-soluble polymer containing carboxyl groups in its molecule and/or a salt thereof can be suitably employed irrespective of whether it is natural, synthetic or semi-synthetic. Illustrative examples of the water-soluble polymer include sodium alginate, polyacrylic acid, sodium polyacrylate, carboxyvinyl polymer, sodium carboxymethylcellulose and gelatin. The amount of the water-soluble polymer which can be added to the hydrophilic base generally ranges from 2% to 50%, preferably from 4% to 25% although it varies depending on its molecular weight, physical properties and the like. In general, amounts smaller than 2% result in weak bases whereas amounts greater than 50% lead to bases having excessively high hardness and hence reduced adhesion to the skin.

As the divalent or trivalent metal salt or the hydrate thereof and/or the divalent or trivalent metal complex (hereinafter called the "multivalent metal salt") which is another one of the components of the above hydrophilic base, their purified products or substances containing them can be used irrespective of whether they are natural or synthetic. Their examples include calcium acetate, calcium phosphate, calcium bis(dihydrogenphosphate), calcium bromide, calcium chloride, calcium citrate, calcium dihydrogenphosphate, calcium monohydrogenphosphate, calcium gluconate, calcium hydroxide, calcium nitrate, calcium tartrate, ammonium aluminum sulfate, aluminum chloride, aluminum hydroxide, aluminum lactate, aluminum nitrate, potassium aluminum sulfate, aluminum silicate, aluminum sulfate, magnesium acetate, magnesium bromide, magnesium carbonate, magnesium chloride, magnesium citrate, magnesium hydroxide, magnesium lactate, magnesium nitrate, magnesium sulfate, magnesium silicate, and magnesium aluminum hydroxide, and hydrates thereof; as well as N-acetyl-L-glutamine aluminum complex and dihydroxy-aluminum aminoacetate. Among these, potassium aluminum sulfate, ammonium aluminum sulfate, magnesium aluminum hydroxide, aluminum hydroxide, N-acetyl-L-glutamine aluminum complex, dihydroxyaluminum aminoacetate and the like can be used suitably. The multivalent metal salt or a substance containing the same can generally be incorporated at a concentration of 0.01–20% in the base, although this amount required in the base varies dependent on the multivalent metal salt and its content in the substance.

Further, the content of water in the hydrophilic base can be 20–90% with 25–80% being preferred. Contents smaller than 20% result in bases having insufficient flexibility, whereas contents greater than 90% result in weak bases. Water contents outside the above range are therefore not preferred.

Examples of hydrophilic bases particularly preferred for use in the present invention include those containing 2–50% of a water-soluble polymer containing carboxyl groups in its molecule and/or a salt thereof [hereinafter called the "component (a)"] as a water-soluble polymer, 0.01–1% of an amino acid-aluminum complex [hereinafter called the "component (b)"] as the multivalent metal salt and 20–90% of water and having a pH of 5.5–8.0.

These hydrophilic bases have extremely good percutaneous absorption enhancing effects compared with other hydrophilic bases and even when no polyoxyethylene nonionic surfactant is incorporated, make it possible to observe practically sufficient percutaneous absorption of piroxicam.

No particular limitation is imposed on the water-soluble polymer containing carboxyl groups in its molecule or its salt as the component (a). It can be used irrespective of whether it is natural, synthetic or semi-synthetic. Examples of the component (a) include sodium alginate, polyacrylic acid, sodium polyacrylate, carboxyvinyl polymer, sodium carboxy-methylcellulose, and gelatin. The component (a) is incorporated at a concentration of 2–50% in the base, with 4–25% being particularly preferred. Concentrations smaller than 2% result in weak bases, whereas concentrations greater than 50% lead to bases having excessively high hardness and hence reduced adhesion to the skin. Contents outside the above range are therefore not preferred.

Examples of the amino acid-aluminum complex as the component (b) include N-acetyl-L-glutamine-aluminum complex and dihydroxyaluminum aminoacetate. The component (b) is incorporated at a concentration of 0.01–1% in the base, with 0.02–0.4% being particularly preferred. Contents smaller than 0.01% result in weak bases, whereas contents greater than 1% result in bases having excessively high hardness and hence reduced adhesion to the skin. Contents outside the above range are therefore not preferred.

To the base of each plaster according to the present invention, it is possible to add components, which are employed in usual bases, as needed in addition to the components described above. These optional components include, for example, known penetration enhancers, humectants, antiseptics, antifungal preservatives, thickeners, self-adhesives, antioxidants, stabilizers, inorganic powders, colorants, flavorants, pH regulators and the like, such as propylene glycol, 1,3-butylene glycol, polyethylene glycol, oleic acid, diisopropyl adipate, diethyl sebacate, isopropyl myristate, crotamiton, benzyl alcohol, medium chain fatty acid triglyceride, glycerin, sodium lactate, D-sorbitol solution, paraoxybenzoate esters, polyvinyl alcohol, dibutylhydroxytoluene, editate disodium, talc, titanium oxide, l-menthol, peppermint oil, citric acid, sodium citrate, tartaric acid, sodium tartrate, phosphoric acid, sodium monohydrogenphosphate, sodium dihydrogenphosphate, ammonia, and alkanolamines.

No particular limitation is imposed on the backing material employed in each anti-inflammatory analgesic plaster according to the present invention, in-sofar as the backing material is a woven fabric, nonwoven fabric, film or sheet having flexibility. Illustrative usable examples include woven or nonwoven fabrics of fibers made of rayon, a polyester, a polyolefin, polyurethane or the like; polymer films; and foamed sheets. They can be used singly, in combination as laminates, or as composite materials such as those laminated with an aluminum foil. Particularly preferred are backing materials having elasticity in all directions. Anchor coating can be applied to them as needed.

No particular limitation is imposed on the manner of having the base spread on the backing material. For example, a prepared base is spread on a backing material and a surface of the base so spread is covered by a protective film, or a base is spread on a protective film and a backing material is then adhered onto the base so spread.

The plaster obtained as described above is placed in a tight container as needed and is then stored.

The present invention will next be described in detail by the following examples. It should however be borne in mind that this invention is by no means limited to or by the examples.

Example 1

To 5 g of polyoxyethylene (9) lauryl ether which had been heated in advance, 0.25 g of piroxicam, 1 g of medium chain fatty acid triglyceride and 0.5 g of l-menthol were added, followed by stirring into an intimate mixture (Component A). To 20 g of glycerin, 3 g of sodium carboxymethylcellulose, 5 g of sodium polyacrylate and 0.15 g of dihydroxyaluminum aminoacetate were added, followed by stirring into an intimate mixture (Component B). In 30 g of purified water which had been heated to 60° C. beforehand, dissolved were 1 g of gelatin, 2 g of polyvinyl alcohol and 0.05 g of editate disodium (Component C).

Components A to C so obtained were charged into a mixer together with a dispersion of 4 g of kaolin in 20 g of D-sorbitol solution (70%) and also 0.1 g of tartaric acid. Purified water was then added to give a total weight of 100 g, followed by stirring into a uniform mixture, whereby 100 g of a piroxicam-containing plaster base were obtained.

The piroxicam-containing plaster base was then spread at an amount of 0.1 g/cm$^2$ on a nonwoven fabric which was made of polyester and polypropylene fibers and weighed 75 g per m$^2$. The surface of the base-spread fabric was covered with a polyester film, whereby an anti-inflammatory analgesic plaster containing 0.25 mg/cm$^2$ of piroxicam was obtained.

Example 2

In a similar manner to Example 1 except that the polyoxyethylene (9) lauryl ether was replaced by 5 g of polyoxyethylene (10) oleyl ether in Component A of the composition shown in Example 1, a piroxicam-containing anti-inflammatory analgesic plaster containing 0.25 mg/cm$^2$ of piroxicam was obtained.

Example 3

In a similar manner to Example 1 except that the polyoxyethylene (9) lauryl ether was replaced by 5 g of polyoxyethylene (10) monostearate, which had been heated and melted in advance, in Component A of the composition shown in Example 1, a piroxicam-containing anti-inflammatory analgesic plaster containing 0.25 mg/cm$^2$ of piroxicam was obtained.

Example 4

In a similar manner to Example 1 except that 5 g of propylene glycol were added to Component A of the composition shown in Example 1, a piroxicam-containing anti-inflammatory analgesic plaster containing 0.25 mg/cm$^2$ of piroxicam was obtained.

Example 5

To 3 g of polyoxyethylene (9) lauryl ether which had been heated in advance, 0.5 g of piroxicam, 1 g of medium chain fatty acid triglyceride and 0.5 g of l-menthol were added, followed by stirring into an intimate mixture (Component A). To 20 g of glycerin, 3 g of sodium carboxymethylcellulose, 5 g of sodium polyacrylate and 0.175 g of dihydroxyaluminum amino-acetate were added, followed by stirring into an intimate mixture (Component B). In 30 g of purified water which had been heated to 60° C. beforehand, dissolved were 1 g of gelatin, 2 g of polyvinyl alcohol and 0.05 g of edetate disodium (Component C).

Components A to C so obtained were charged into a mixer together with a dispersion of 4 g of kaolin in 20 g of D-sorbitol solution (70%) and also 0.4 g of tartaric acid. Purified water was then added to give a total weight of 100 g, followed by stirring into a uniform mixture, whereby 100 g of a piroxicam-containing plaster base were obtained.

The piroxicam-containing plaster base was then spread at an amount of 0.1 g/cm$^2$ on a 100 g/m$^2$ nonwoven fabric made of polyester and polypropylene fibers. The surface of the base-spread fabric was covered with a polypropylene film, whereby a piroxicam-containing anti-inflammatory analgesic plaster containing 0.5 mg/cm$^2$ of piroxicam was obtained.

Example 6

To 3 g of polyoxyethylene (9) lauryl ether, which had been heated in advance, 0.25 g of piroxicam, 1 g of medium chain fatty acid triglyceride and 0.5 g of l-menthol were added, followed by stirring into an intimate mixture (Component A). To 20 g of glycerin, 3 g of sodium carboxymethylcellulose, 5 g of sodium polyacrylate and 0.15 g of dihydroxyaluminum amino-acetate were added, followed by stirring into an intimate mixture (Component B). in 30 g of purified water which had been heated to 60° C. beforehand, dissolved were 1 g of gelatin, 2 g of polyvinyl alcohol and 0.05 g of edetate disodium (Component C).

Components A to C so obtained were charged into a mixer together with a dispersion of 4 g of kaolin in 20 g of D-sorbitol solution (70%) and also 0.4 g of tartaric acid. Purified water was then added to give a total weight of 100 g, followed by stirring into a uniform mixture, whereby 100 g of a piroxicam-containing plaster base were obtained.

The piroxicam-containing plaster base was then spread at an amount of 0.1 g/cm$^2$ on a 100 g/m$^2$ nonwoven fabric made of polyester and polypropylene fibers. The surface of the base-spread fabric was covered with a polypropylene film, whereby a piroxicam-containing anti-inflammatory analgesic plaster containing 0.25 mg/cm$^2$ of piroxicam was obtained.

Example 7

To 3 g of polyoxyethylene (9) lauryl ether which had been heated in advance, 0.75 g of piroxicam, 1 g of medium chain fatty acid triglyceride and 0.5 g of l-menthol were added, followed by stirring into an intimate mixture (Component A). To 20 g of glycerin, 3 g of sodium carboxymethylcellulose, 5 g of sodium polyacrylate and 0.175 g of dihydroxyaluminum amino-acetate were added, followed by stirring into an intimate mixture (Component B). In 30 g of purified water which had been heated to 60° C. beforehand, dissolved were 1 g of gelatin, 2 g of polyvinyl alcohol and 0.05 g of edetate disodium (Component C).

Components A to C so obtained were charged into a mixer together with a dispersion of 4 g of kaolin in 20 g of D-sorbitol solution (70%) and also 0.4 g of tartaric acid. Purified water was then added to give a total weight of 100 g, followed by stirring into a uniform mixture, whereby 100 g of a piroxicam-containing plaster base were obtained.

The piroxicam-containing plaster base was then spread at an amount of 0.1 g/cm$^2$ on a 100 g/m$^2$ nonwoven fabric made of polyester and polypropylene fibers. The surface of the base-spread fabric was covered with a polypropylene film, whereby a piroxicam-containing anti-inflammatory analgesic plaster containing 0.75 mg/cm$^2$ of piroxicam was obtained.

Example 8

To 20 g of glycerin, 5 g of piroxicam were added, followed by stirring. To the resulting mixture, 3 g of sodium carboxymethylcellulose, 5 g of sodium polyacrylate and 0.1 g of dihydroxyaluminum aminoacetate were added, followed by stirring into an intimate mixture (Component A). In 10 g of D-sorbitol solution (70%), 4 g of kaolin were uniformly dispersed (Component B). In 30 g of purified water which had been heated beforehand, 1 g of gelatin was dissolved (Component C).

Components A to C so obtained were charged into a mixer together with 3.5 g of a 10% aqueous solution of polyacrylic acid, 5 g of polyoxyethylene (10) monolaurate and 0.05 g of edetate disodium. Purified water was then added to give a total weight of 100 g, followed by stirring into a uniform mixture, whereby 100 g of a piroxicam-containing plaster base were obtained.

The piroxicam-containing plaster base so obtained was then spread at an amount of 0.05 g/cm$^2$ on a polyester film. The surface of the base-spread film was covered with a sheet which was a laminate of a 30-μm thick polyurethane film and a 10g/m$^2$ nonwoven fabric made of rayon fibers, whereby an anti-inflammatory analgesic plaster containing 2.5 mg/cm$^2$ of piroxicam was obtained.

Example 9

To 8 g of polyoxyethylene (15) oleyl ether which had been heated in advance, 5 g of propylene glycol, 0.1 g of methyl paraoxybenzoate, 0.05 g of propyl paraoxybenzoate and 1.0 g of piroxicam were added, followed by stirring. To the resulting mixture, 10 g of glycerin, 3 g of sodium carboxymethylcellulose, 4 g of sodium polyacrylate and 0.2 g of dihydroxyaluminum aminoacetate were added, followed by stirring into an intimate mixture (Component A). In 35 g of D-sorbitol solution (70%), 4 g of kaolin were uniformly dispersed (Component B).

Components A and B so obtained were charged into a mixer together with 0.4 g of tartaric acid. Purified water was then added to give a total weight of 100 g, followed by stirring into a uniform mixture, whereby 100 g of a piroxicam-containing plaster base were obtained.

The piroxicam-containing plaster base so obtained was then spread at an amount of 0.1 g/cm$^2$ on a 80 g/m$^2$ nonwoven fabric made of rayon fibers. The surface of the base-spread fabric was covered with a polyester film, whereby a piroxicam-containing anti-inflammatory analgesic plaster containing 1.0 mg/cm$^2$ of piroxicam was obtained.

Example 10

To 15 g of glycerin, 4.5 g of sodium polyacrylate, 2.5 g of sodium carboxymethylcellulose and 0.15 g of N-acetyl-L-glutamine aluminum were added, followed by stirring into an intimate mixture (Component A). In 20.0 g of purified water which had been heated in advance, 1 g of gelatin was dissolved (Component B). To 3.0 g of a heated mixture of polyoxyethylene (10) behenyl ether and 1.0 g of medium chain fatty acid triglyceride, 0.25 g of piroxicam was added, followed by stirring into an intimate mixture (Component C).

Components A to C so obtained were charged into a mixer together with 2 g of kaolin, 0.8 g of tartaric acid and 20 g of D-sorbitol (70%). Purified water was then added to give a total weight of 100 g, followed by stirring into a uniform mixture, whereby 100 g of a piroxicam-containing plaster base were obtained.

The piroxicam-containing plaster base so obtained was then spread at an amount of 0.1 g/cm$^2$ on a 80 g/m$^2$ nonwoven fabric made of polypropylene fibers. The surface of the base-spread fabric was covered with a polypropylene film, whereby a piroxicam-containing anti-inflammatory analgesic plaster containing 0.25 mg/cm$^2$ of piroxicam was obtained.

Example 11

To 20 g of glycerin, 5 g of sodium polyacrylate, 3 g of sodium carboxymethylcellulose and 0.15 g of dihydroxyaluminum aminoacetate were added, followed by stirring into an intimate mixture (Component A). In 20.0 g of purified water which had been heated in advance, 1 g of gelatin and 2 g of polyvinyl alcohol were dissolved (component B). After 5 g of polyoxyethylene (10) monooleate and 1 g of medium chain fatty acid triglyceride were heated, 0.25 g of piroxicam was added, followed by stirring into an intimate mixture (Component C).

Components A to C so obtained were charged into a mixer together with 4 g of kaolin, 0.1 g of tartaric acid and 20.0 g of D-sorbitol solution (70%). Purified water was then added to give a total weight of 100 g, followed by stirring into a uniform mixture, whereby 100 g of a piroxicam-containing plaster base were obtained.

The piroxicam-containing plaster base so obtained was then spread at an amount of 0.1 g/cm$^2$ on a 100 g/m$^2$ nonwoven fabric made of polyester and polypropylene fibers. The surface of the base-spread fabric was covered with a polypropylene film, whereby a piroxicam-containing anti-inflammatory analgesic plaster containing 0.25 mg/cm$^2$ of piroxicam was obtained.

Example 12

To a mixture of 5 g of propylene glycol and 5 g of glycerin, 5 g of sodium polyacrylate and 0.3 g of N-acetyl-L-glutamine aluminum were added, followed by stirring into an intimate mixture (Component A). In 40.0 g of purified water which had been heated in advance, 3 g of carboxyvinyl polymer were added under vigorous stirring into an intimate mixture (Component B). To 8 g of polyoxyethylene (9) lauryl ether, 0.5 g of 1-menthol, 0.3 g of medium chain fatty acid triglyceride and 4.0 g of piroxicam were added, followed by stirring into an intimate mixture (Component C). In 12.85 g of purified water which had been heated beforehand, 1 g of gelatin and 0.05 g of editate disodium were dissolved (Component D).

Components A to D so obtained were stirred in a mixer together with 15 g of D-sorbitol solution (70%) into an intimate mixture, whereby 100 g of a piroxicam-containing plaster base were obtained.

The piroxicam-containing plaster base so obtained was then spread at an amount of 0.025 g/cm$^2$ on a 20 g/m$^2$ nonwoven fabric made of polypropylene fibers. The surface of the base-spread fabric was covered with a polypropylene film, whereby a piroxicam-containing anti-inflammatory analgesic plaster containing 1.0 mg/cm$^2$ of piroxicam was obtained.

Referential Example 1

As shown in Table 1, various plaster bases of different pH values were prepared.

Namely, each plaster base was prepared in the following manner: To 15 g of glycerin, 0.25 g of piroxicam was added, followed by stirring. To the resulting mixture, 4 g of sodium carboxymethylcellulose, 5 g of sodium polyacrylate and 0.1 g of dihydroxyaluminum aminoacetate were added, followed by stirring into an intimate mixture (Component A). In 50 g of purified water which had been heated in advance, 1 g of gelatin, 1 g of polyoxyethylene (60) hydrogenated castor oil and 0.05 g of editate disodium were dissolved (Component B).

Components A and B so obtained were charged into a mixer together with 4 g of kaolin and tartaric acid in the corresponding amount shown in Table 1. Purified water was then added to give a total weight of 100 g, followed by stirring into a uniform slurry, whereby 100 g of a piroxicam-containing plaster base were obtained.

The piroxicam-containing plaster base so obtained was then spread at an amount of 0.1 g/cm$^2$ on a 75 g/m$^2$ nonwoven fabric made of polyester, polypropylene and rayon fibers. The surface of the base-spread fabric was covered with a polyester film.

Piroxicam-containing anti-inflammatory analgesic plasters a, b, c and d, which contained 0.25 mg/cm$^2$ of piroxicam, were obtained.

TABLE 1

| | (a) | (b) | (c) | (Unit: g) (d) |
|---|---|---|---|---|
| Piroxicam | 0.25 | 0.25 | 0.25 | 0.25 |
| Glycerin | 15.00 | 15.00 | 15.00 | 15.00 |
| Polyoxyethylene (60) hydrogenated castor oil | 1.00 | 1.00 | 1.00 | 1.00 |
| Sodium carboxy-methylcellulose | 4.00 | 4.00 | 4.00 | 4.00 |
| Sodium polyacrylate | 5.00 | 5.00 | 5.00 | 5.00 |
| Gelatin | 1.00 | 1.00 | 1.00 | 1.00 |
| Kaolin | 4.00 | 4.00 | 4.00 | 4.00 |
| Dihydroxyaluminum aminoacetate | 0.10 | 0.10 | 0.10 | 0.10 |
| Tartaric acid | 0.05 | 0.45 | 0.80 | 1.20 |
| Editate disodium | 0.05 | 0.05 | 0.05 | 0.05 |
| Purified water | 69.55 | 69.15 | 68.80 | 68.40 |
| Total | 100.00 | 100.00 | 100.00 | 100.00 |
| PH | 7.6 | 6.8 | 6.2 | 5.6 |

Comparative Example 1

A piroxicam plaster containing 0.25 mg/cm$_2$ of piroxicam was obtained in a similar manner to Example 1 except for the omission of polyoxyethylene (9) lauryl ether.

Comparative Example 2

A piroxicam plaster containing 0.25 mg/cm$^2$ of piroxicam was obtained in a similar manner to Example 2 except that 5 g of polyoxyethylene (2) oleyl ether were added instead of 5 g of polyoxyethylene (10) oleyl ether in Component A of the composition shown in Example 2.

Comparative Example 3

A piroxicam plaster containing 0.25 mg/cm$^2$ of piroxicam was obtained in a similar manner to Example 2 except that 5 g of polyoxyethylene (20) oleyl ether were added instead of 5 g of polyoxyethylene (10) oleyl ether in Component A of the composition shown in Example 2.

Referential Comparative Example

In a similar manner to Referential Example 1 except for the addition of 1.85 g of tartaric acid, a piroxicam plaster containing 0.25 mg/cm$^2$ of piroxicam and having a pH of 5.2 was obtained.

Test 1

The piroxicam-containing anti-inflammatory analgesic plasters prepared in Examples 1 to 3 and the piroxicam-containing plasters prepared in Comparative Examples 1 to 3 were each applied to the shaved backs (30 cm$^2$) of male guinea pigs (species: Hartley, age: 4 weeks old, body weight: 250–300 g). From each guinea pig, blood samples were collected through a cannula inserted in the jugular vein before the application of the plaster and upon elapsed times of 2, 4, 6 and 8 hours after the application of the plaster. The plasma concentrations of piroxicam in the respective blood samples were measured by HPLC, whereby changes in the plasma concentration of piroxicam were observed. The results are diagrammatically shown in FIG. 1.

As is apparent from FIG. 1, the plasma concentration of piroxicam after application of the piroxicam-containing plaster of Comparative Example 1, said plaster containing no polyoxyethylene nonionic surfactant, was about 10 ng/ml upon an elapsed time of 6–8 hours after application, whereas the plasma concentration of piroxicam after application of the piroxicam-containing anti-inflammatory analgesic plaster according to the present invention obtained in Example 1, said plaster containing 5% of polyoxyethylene (9) lauryl ether, that is, a polyoxyethylene nonionic surfactant containing 9 moles of added ethylene oxide, was 64 ng/ml upon elapsed time of 8 hours after application, the plasma concentration of piroxicam after application of the piroxicam-containing anti-inflammatory analgesic plaster according to the present invention obtained in Example 2, said plaster containing 5% of polyoxyethylene (10) oleyl ether, that is, a polyoxyethylene nonionic surfactant containing 10 moles of added ethylene oxide, was 42 ng/ml upon elapsed time of 8 hours after application, and the plasma concentration of piroxicam after application of the piroxicam-containing anti-inflammatory analgesic plaster according to the present invention obtained in Example 3, said plaster containing 5% of polyoxyethylene (10) monostearate, that is, a polyoxyethylene nonionic surfactant containing 10 moles of added ethylene oxide, was 54 ng/ml upon elapsed time of 8 hours after application, whereby the plasma concentration of piroxicam after application of the plasters of Examples 1–3 were all very high. Further, the plasma concentration of piroxicam after application of the piroxicam-containing plasters of Comparative Examples 2 and 3—which contained 5% of polyoxyethylene (2) oleyl ether and polyoxyethylene (20) oleyl ether, that is, polyoxyethylene nonionic surfactants containing 2 and 20 moles of added ethylene oxide, respectively—were about 10 ng/ml upon an elapsed time of 6–8 hours after application.

Test 2

The piroxicam-containing anti-inflammatory analgesic plasters (a) to (d) prepared in Referential Example 1 and the piroxicam-containing plasters prepared in Referential Comparative Example were each applied to the shaved backs (30 cm$^2$) of male guinea pigs (species: Hartley, age: 5 weeks old, body weight: 300–350 g). Each of the places where the plasters were applied was covered with "SARAN Wrap" (trade mark; a polyvinylidene chloride film; product of Asahi Chemical Industry Co., Ltd.). From each guinea pig, blood samples were collected through a cannula inserted in the jugular vein before the application of the plaster and upon elapsed times of 2, 4, 6 and 8 hours-after the application of the plaster. The piroxicam concentrations in the plasmas of the respective blood samples were measured by HPLC, whereby changes in the piroxicam concentration in plasma were observed. The results are diagrammatically shown in FIG. 2.

As is clearly envisaged from FIG. 2, the plasma concentration of piroxicam after application of the piroxicam-containing plaster of the Referential Comparative Example in which the pH of the base was 5.2 was lower than 10 ng/ml, that is, the measurable lower limit of the plasma concentration of piroxicam, whereas the plasma concentration of piroxicam after application of the piroxicam-containing anti-inflammatory analgesic plasters of Referential Examples 1a–1d in which the bases had a pH of 5.5 or higher showed an apparently higher plasma concentration of piroxicam. It is hence understood that a base having a pH of 5.5 or higher shows good percutaneous absorption of piroxicam.

We claim:

1. An anti-inflammatory analgesic plaster carrying thereon a base comprising:

i) piroxicam;
   ii) a polyoxyethylene non-ionic surfactant having 5–15 moles of added ethylene oxide; and
   iii) a hydrophilic base comprising:
      a) a water-soluble polymer;
      b) a divalent or tri-valent metal salt, or a hydrate thereof, and/or a divalent or tri-valent metal complex; and
      c) water.

2. An anti-inflammatory analgesic plaster according to claim 1, wherein the content of the polyoxyethylene non-ionic surfactant in the base ranges from 1 wt. % to 20 wt. %.

3. An anti-inflammatory analgesic plaster according to claim 1, wherein said hydrophilic base has a pH of from 5.5 to 8.0.

4. The anti-inflammatory analgesic plaster of claim 1, comprising 0.05–5 wt. % based on said base of piroxicam.

5. The anti-inflammatory analgesic plaster of claim 1, comprising 0.1–2 wt. % based on said base of piroxicam.

6. The anti-inflammatory analgesic plaster of claim 1, comprising 2–10 wt. % based on said base of said polyoxyethylene non-ionic surfactant.

7. The anti-inflammatory analgesic plaster of claim 1, wherein said hydrophilic base comprises from 2–50 wt. % based on said hydrophilic base, of said water-soluble polymer.

8. The anti-inflammatory analgesic plaster of claim 1, wherein said hydrophilic base comprises 4–25 wt. % based on said hydrophilic base, of said water-soluble polymer.

9. The anti-inflammatory analgesic plaster of claim 1, wherein said hydrophilic base comprises 20–90 wt. % based on said hydrophilic base, of water.

10. The anti-inflammatory analgesic plaster of claim 2, wherein said hydrophilic base has a pH of from 5.5 to 8.0.

* * * * *